US012606690B2

(12) United States Patent
DiPucchio et al.

(10) Patent No.: US 12,606,690 B2
(45) Date of Patent: Apr. 21, 2026

(54) BASE-MEDIATED METHOD FOR THE RECYCLING OF EPOXY RESIN-CARBON FIBER COMPOSITES

(71) Applicant: Alliance for Energy Innovation, LLC, Golden, CO (US)

(72) Inventors: Rebecca Claire DiPucchio, Wheat Ridge, CO (US); Katherine Rose Stevenson, Wheat Ridge, CO (US); Gregg Tyler Beckham, Golden, CO (US)

(73) Assignee: Alliance for Energy Innovation, LLC, Golden, CO (US)

( * ) Notice: Subject to any disclaimer, the term of this patent is extended or adjusted under 35 U.S.C. 154(b) by 448 days.

(21) Appl. No.: 18/383,458

(22) Filed: Oct. 24, 2023

(65) Prior Publication Data

US 2024/0158603 A1 May 16, 2024

Related U.S. Application Data

(60) Provisional application No. 63/418,874, filed on Oct. 24, 2022.

(51) Int. Cl.
*C08J 11/24* (2006.01)
*C07C 37/52* (2006.01)

(52) U.S. Cl.
CPC ............... *C08J 11/24* (2013.01); *C07C 37/52* (2013.01); *C08J 2363/10* (2013.01)

(58) Field of Classification Search
CPC ........ C08J 11/24; C08J 2363/10; C07C 37/52
See application file for complete search history.

(56) References Cited

PUBLICATIONS

Ahrens et al., "Catalytic Disconnection of C—O Bonds in Epoxy Resins and Composites", Feb. 2021, available at https://assets.researchsquare.com/files/rs-1990090/v1_covered.pdf?c=1661794691, accessed on Jan. 23, 2024, pp. 1-16.
Jiang et al., "On the successful chemical recycling of carbon fiber/epoxy resin composites under the mild condition", Composites Science and Technology, Oct. 2017, vol. 151, pp. 243-251.
Liu et al., "Mild chemical recycling of aerospace fiber/epoxy composite wastes and utilization of the decomposed resin", Polymer Degradation and Stability, May 2017, vol. 139, pp. 20-27.
Lo et al., "Recycling Benzoxazine-Epoxy Composites via Catalytic Oxidation", ACS Sustainable Chemistry & Engineering, 2018, vol. 6, No. 6, pp. 7227-7231.
Long et al., "A mild and efficient oxidative degradation system of epoxy thermosets: full recovery and degradation mechanism", Green Chemistry, 2022, vol. 24, No. 18, pp. 7082-7091.
Ma et al., "Chemical treatment for recycling of amine/epoxy composites at atmospheric pressure", Polymer Degradation and Stability, Jul. 2018, vol. 153, pp. 307-317.
Navarro et al., "Mechanism and Catalysis of Oxidative Degradation of Fiber-Reinforced Epoxy Composites", Topics in Catalysis, 2018, vol. 61, pp. 704-709.
Wang et al., "Chemical Recycling of Carbon Fiber Reinforced Epoxy Resin Composites via Selective Cleavage of the Carbon-Nitrogen Bond", ACS Sustainable Chemistry & Engineering, 2015, vol. 3, No. 12, pp. 3332-3337.
Zhao et al., "Efficient recycling of carbon fibers from amine-cured CFRP composites under facile condition", Polymer Degradation and Stability, Sep. 2020, vol. 179, No. 109268, pp. 1-9.

*Primary Examiner* — Sikarl A Witherspoon
(74) *Attorney, Agent, or Firm* — Sam J. Barkley

(57) ABSTRACT

Methods, compositions of matter and processes for a base-mediated chemical deconstruction of varying amine-cured epoxy resins into constituent monomer alcohol products and amine materials are disclosed herein.

20 Claims, 8 Drawing Sheets

A

B

C

1

2 or 3

2, *N*-arlyamine
3, *N*-cyclohexylamine

A

1:1 Aniline:BADGE (6)
7, Quantitative

B

1:1 Cyclohexylamine:BADGE (6)
8, Quantitative

C 0.5:0.5:1 Aniline:Cyclohexylamine:BADGE (6)
9, Quantitative 0.75:0.25:1 Aniline:Cyclohexylamine:BADGE (6)
10, Quantitative 0.9:0.1:1 Aniline:Cyclohexylamine:BADGE (6)
11, Quantitative

12

1) 3 mL Dioxane, 1 h, 200 °C, MW.
2) 4 eq. KOtBu, 1:2 Toluene:Dioxane
v/v 160 °C, 48 h
3) 2 M HCl in Et₂O 71±10 % Yield

BASE-MEDIATED METHOD FOR THE RECYCLING OF EPOXY RESIN-CARBON FIBER COMPOSITES

CROSS-REFERENCE TO RELATED APPLICATIONS

This application claims priority under 35 U.S.C. § 119 to U.S. provisional patent application no. 63/418,874 filed on 24 Oct. 2023, the contents of which are hereby incorporated in their entirety.

CONTRACTUAL ORIGIN

The United States Government has rights in this invention under Contract No. DE-AC36-08G028308 between the United States Department of Energy and Alliance for Sustainable Energy, LLC, the Manager and Operator of the National Renewable Energy Laboratory.

BACKGROUND

Carbon fiber-reinforced epoxy composites are used as lightweight components in a variety of products ranging from wind turbine blades to structural components in airplanes and vehicles.1 Carbon fiber costs range from $20-40/kg for lower strength applications or up to $175/kg in aviation-specific applications. Production of these materials requires substantial energy inputs, which in turn generates 43 kg $CO_2$e/kg of new fiber during typical US carbon fiber manufacturing. The substantial energy and GHG emissions associated with carbon fiber production and the lack of recycling options together have motivated the development of strategies for carbon fiber recovery. Meanwhile, epoxy resins comprise about 50 wt percent of carbon fiber composite materials, and global demand for these resins was 4 million metric tons in 2020. Epoxies on their own are primarily used in construction, coatings, and electronics. Production of epoxy thermosets results in 4.6 $CO_2$e/kg of new resin.

Current disposal of composite waste usually in-volves landfilling, pyrolysis, or grinding composites for use in applications that can tolerate lower quality mechanical properties. Emerging chemical recycling strategies to deconstruct composite waste materials are often based on Lewis acidic, strong Bronsted acid, oxidative, or ionic liquid-based reactions. A relatively new contribution employs a homogeneous, reductive Ru-based catalyst. Work to date has primarily focused on recycling carbon fiber, including assessment of post-recovery mechanical properties of the fibers. However, the epoxy portion of these composites also represents a substantial amount of unrecovered carbon, encouraging opportunities to recover epoxy monomers while still maintaining carbon fiber strength and alignment.

To date, chemical recycling strategies specific to amine-cured resins are primarily limited to strong acids or oxidants. Amine-cured epoxies represent the epoxy component of some of the strongest and more widely used composite materials. These resins are more challenging to depolymerize relative to their anhydride-cured material counterparts, the latter which are linked via ester bonds, for which a variety of catalytic strategies exist. Conversely, amine-epoxy systems contain ether and amine linkages between monomers (see FIG. 1). Using tetrafunctional amine-based curing agents also results in a more densely crosslinked network than difunctional alcohol monomers. In addition, these epoxies are often proprietary structures that vary in composition based on the intended application. As a result, literature contributions in epoxy recycling tend to either use industry samples or generate their own crosslinked networks. Overall, efforts in epoxy recycling would benefit from improved substrate characterization, such that deconstruction reactions can be better understood and development of more efficient depolymerization processes will be accelerated.

SUMMARY

In an aspect, disclosed herein are methods, compositions of matter and processes useful for a base-mediated technology for chemical deconstruction of varying amine-cured epoxy resins into constituent monomer alcohol products and amine materials. Processes disclosed herein result in simultaneous epoxy and carbon fiber recovery from composites and allows for recovery of previously ignored components of epoxy resin from resin-fiber composites.

In an aspect, disclosed herein is a method for metal alkoxide base-mediated cleavage of C—O and C—N bonds in amine-cured epoxy resins comprising contacting an amine-cured epoxy resin with a metal alkoxide base. In an embodiment, the metal alkoxide base comprises potassium tert-butoxide. In an embodiment, a metal hydroxide base is added to the metal alkoxide base wherein the metal hydroxide base is selected from the group consisting of LiOH, NaOH, KOH, $Ca(OH)_2$, and $Sr(OH)_2$. In an embodiment, the cleavage of C—O and C—N bonds in amine-cured epoxy resins yields about 97 percent molar yield of phenols and about 99 percent molar yield of amine products. In an embodiment, the metal alkoxide base-mediated cleavage of C—O and C—N bonds in amine-cured epoxy resins occurs at a temperature of from about 140 degrees Celsius to about 160 degrees Celsius. In an embodiment, the metal alkoxide base-mediated cleavage of C—O and C—N bonds in amine-cured epoxy resins occurs in a solvent mixture of toluene and dioxane. In an embodiment, the metal alkoxide base-mediated cleavage occurs over about 48 hours. In an embodiment, the method further comprises swelling the amine-cured epoxy resin before contacting the resin with the metal alkoxide base. In an embodiment, the amine-cured epoxy resin is BADGE. In an embodiment, the method further comprises the step of isolating BPA and aniline as products resulting from the metal alkoxide base-mediated cleavage of C—O and C—N bonds of BADGE. In an embodiment, the metal alkoxide base is potassium tert-butoxide. In an embodiment, the method further comprises swelling the BADGE before contacting the BADGE with the metal alkoxide base. In an embodiment, the amine-cured epoxy resin is a thermoplastic resin. In an embodiment, the metal alkoxide base is potassium tert-butoxide. In an embodiment, the method further comprises swelling the thermoplastic resin before contacting the thermoplastic resin with the metal alkoxide base. In an embodiment, the amine-cured epoxy resin is a thermoset resin. In an embodiment, the metal alkoxide base is potassium tert-butoxide. In an embodiment, the thermoset resin has a glass temperature transition of about 110 degrees Celsius. In an embodiment, the method further comprises isolating resulting monomeric reaction products. In an embodiment, the method further comprises swelling the thermoset resin before contacting the thermoset resin with the metal alkoxide base.

Other objects, advantages, and novel features of the present invention will become apparent from the following detailed description of the invention when considered in conjunction with the accompanying drawings.

BRIEF DESCRIPTION OF THE DRAWINGS

FIG. 1A depicts epoxy anhydrides, FIG. 1B depicts aliphatic epoxy amines, and FIG. 1C depicts aromatic epoxy amine networks. In all cases, bonds targeted for cleavage are highlighted in red.

DETAILED DESCRIPTION

Figure 1A:
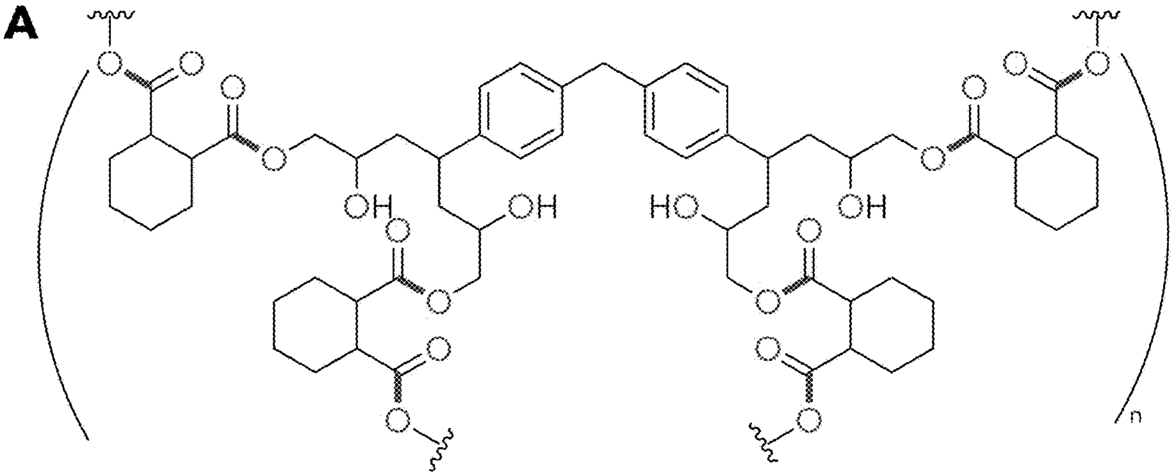
FIGS. 1A, 1B and 1C depict general examples of epoxy resin structures.
Figure 1B:
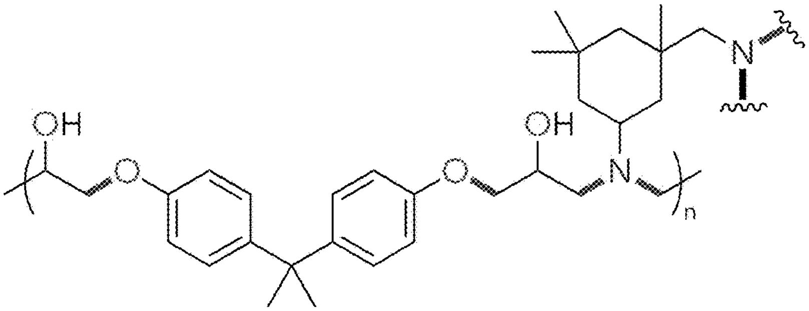
Figure 1C:
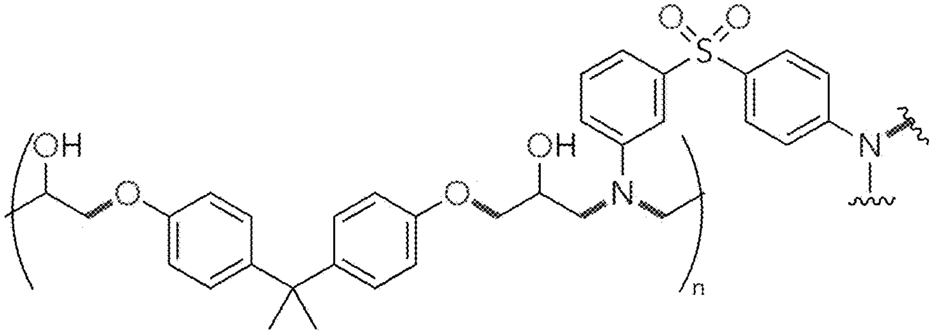

Carbon fiber-reinforced epoxy composites are used in multiple industries, including for aerospace, automotive, and wind energy applications, due to their excellent strength-to-weight ratios and tunable material properties. Fortunately, recycling strategies for carbon fiber-based composites are emerging, with the primary focus on recovery of fibers due to the cost and energy intensity in their production. In addition to fiber recovery, there is an opportunity to recycle the epoxy components, such that ideal recycling strategies would yield both post-consumer fibers and epoxy monomers for reuse. To that end, here we disclose methods for potassium tert-butoxide-mediated cleavage of C—O and C—N bonds in amine-cured epoxy resins.

Open-loop chemical recycling methods for amine-cured epoxy resins and carbon fiber composites should ideally cleave C—O and/or C—N bonds to generate useful monomers. With this motivation, here we disclose a potassium tert-butoxide (KOtBu)-mediated strategy for depolymerization of amine-cured epoxy resins developed via reactions with aromatic and aliphatic amine-based model compounds. Using metal alkoxide bases as reagents for deconstruction resulted in valuable monomer products from simultaneous C—O and C—N cleavage, and these reagents also play a key role in maintaining high monomer yields. Reactions with model epoxy thermoplastics were used to inform reaction conditions on both model and industrially-motivated amine-cured epoxy thermosets. The bottom-up approach in this work also presents well characterizes model substrates of multiple complexities for depolymerization studies.

In an embodiment, chemical deconstruction of varying amine-cured epoxy resins is accomplished via developing model compounds that reflect both C—O and C—N linkages in amine-cured epoxy composites, before expanding to both model linear thermoplastics and thermosets. We obtain excellent yields of both phenol (up to 97% molar yield) and amine products (up to 99 mol percent) from aromatic and/or aliphatic amine-based model compounds. This system enables up to quantitative yield of bisphenol-A and up to 58% molar yield of aniline from model thermoplastic epoxy amines and 71% molar yield of BPA from a reaction with a thermoset substrate. These data correspond to 15% mass recovery of BPA from a commercial epoxy thermoset.

Disclosed herein are methods, compositions of matter and processes useful for a base-mediated technology for chemical deconstruction of varying amine-cured epoxy resins into constituent monomer alcohol products and amine materials. Processes disclosed herein result in simultaneous epoxy and carbon fiber recovery from composites and allows for recovery of previously ignored components of epoxy resin from resin-fiber composites. Such resin monomers can be used to make new resins or other types of prevalent plastics.

Disclosed herein are methods for using structurally accurate model compounds to assess bond-breaking events in epoxy resin networks and using the acquired data to recycle multiple types of amine-cured model polymers. Shifting reaction strategies away from acidic or oxidative catalysts and towards basic systems has improved product stabilities without involving complex catalyst syntheses. Disclosed herein are polymer syntheses to model compound deconstruction reactions, preliminary mechanistic investigations, and depolymerization results. Using methods disclosed herein, understanding epoxy structure can lead to excellent monomer yields for previously unrecoverable reaction components.

Methods disclosed herein can rigorously synthesize and deconstruct epoxy thermoplastics based on either aliphatic or aromatic amines or a combination thereof.

Using methods disclosed herein, deconstruction requires excess base (KOtBu for best results, but others work), heat (140-200° C.), and reaction times of 1-48 hr as dependent on the substrate.

In certain embodiments, disclosed herein are recycling thermoset (crosslinked) versions of these resins, but the chemical structures of repeat units are very similar to what we already recycle.

Disclosed herein are methods to directly deconstruct these thermoplastics to BPA as an immediate product (up to 70% yield by GC-FID) with the only required workup being an acidic neutralization step.

These deconstruction reactions generate a small amount of pressure but do not require air sensitive reagents or any added pressure, they can be setup in air and without extra dry solvents/reagents.

Materials and Instrumentation

Potassium tert-butoxide (Sigma-Aldrich), 1,2-epoxy-3-phenoxypropane (Sigma-Aldrich), N-ethylaniline (Sigma-Aldrich), N-ethylcyclohexylamine (Sigma-Aldrich), bisphenol a diglycidyl ether (Sigma-Aldrich), aniline (Sigma-Aldrich), cyclohexylamine (TCI Chemicals), isophorone diamine (TCI Chemical), and 4,4'-diaminodiphenylsulfone (EMD Millipore) were used as received.

$^1$H NMR spectra were recorded on Bruker 300 MHz spectrometers at ambient temperature. Gas chromatograms of starting materials and resultant products were recorded on an Agilent 7890A GC System. Polymer characterizations were conducted using TA Discovery Series TGA 5500, TA Discovery Series DSC25, Agilent 1260 Infinity II GPC, and Perkin Elmer FT-IR Spectrometer. 20 mL microwave vials used were purchased from Biotage. 3 mL sand bath reactors were purchased from Swagelok.

Model Compound Syntheses and Characterization

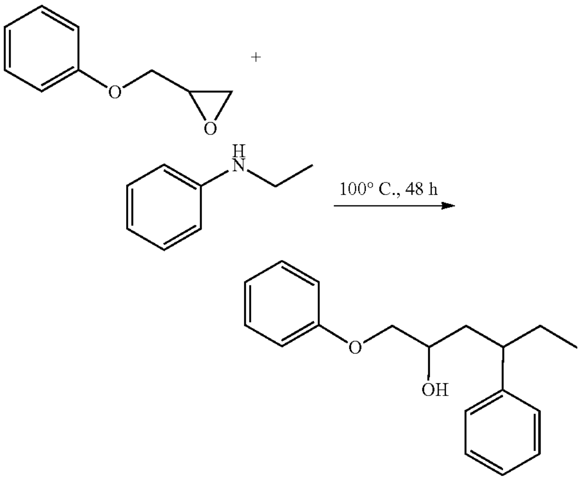

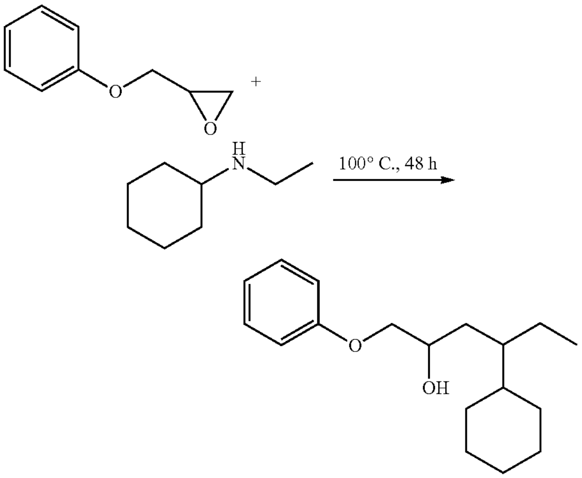

Thermoplastic Syntheses and Characterization

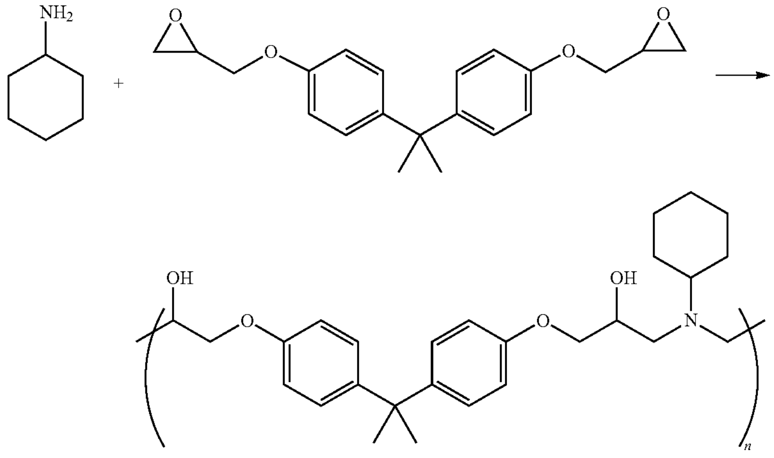

-continued
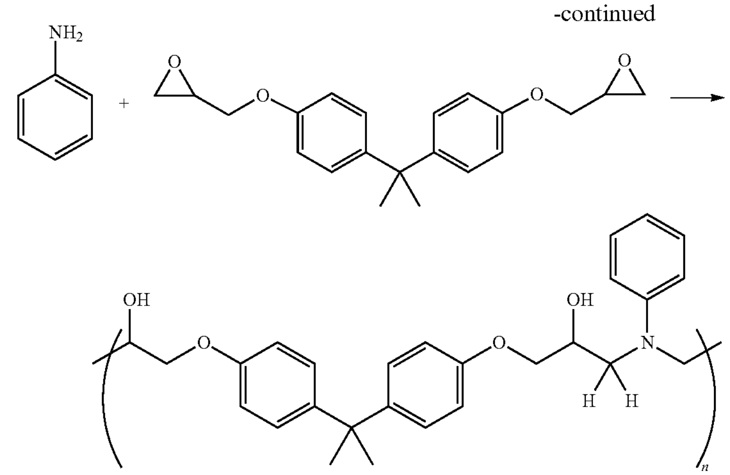
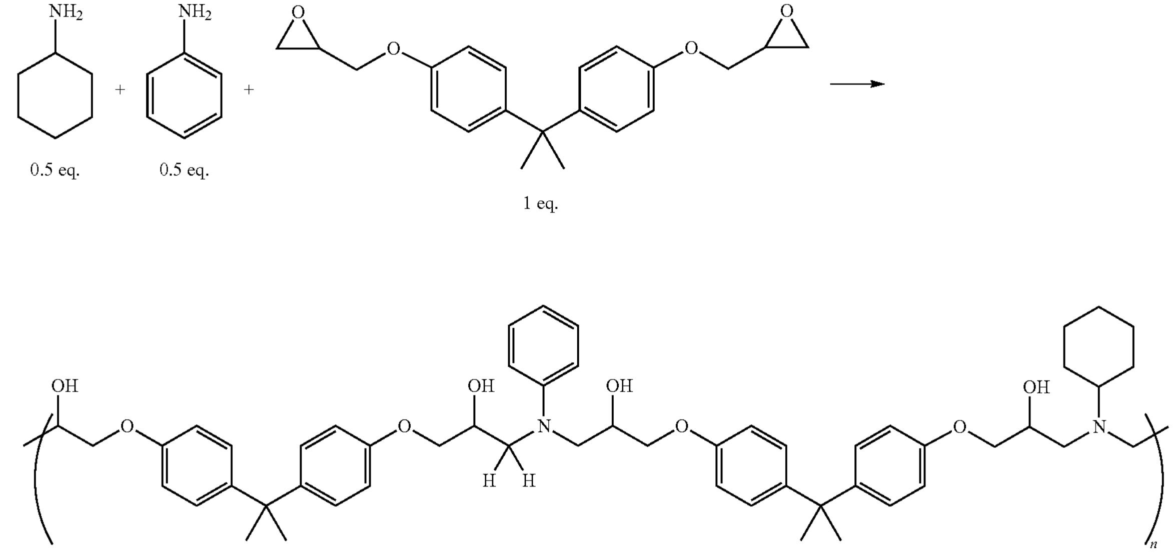
Thermoset Syntheses and Characterization
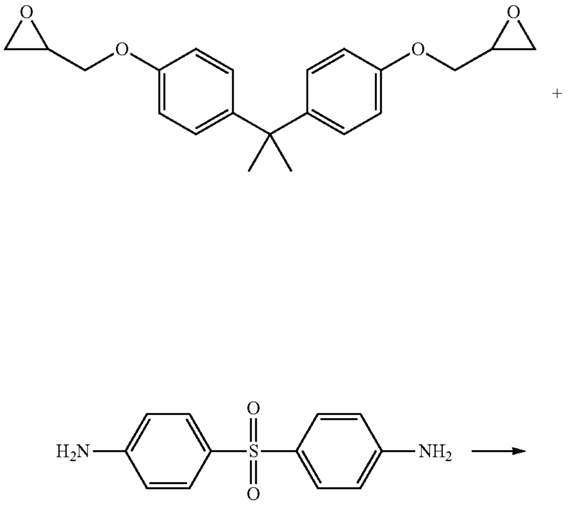
-continued
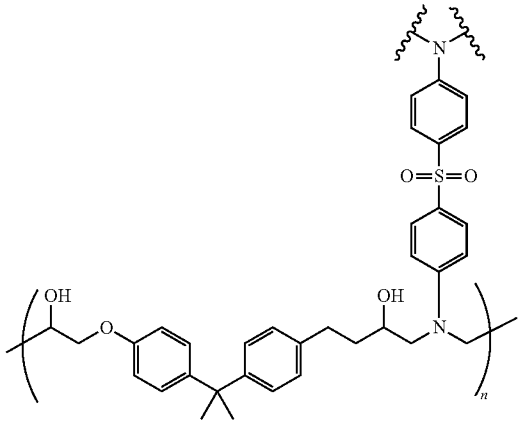
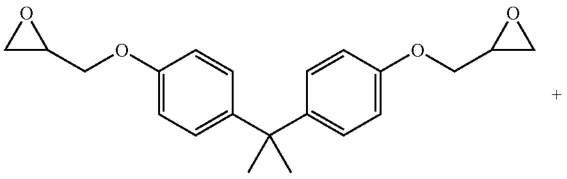

-continued

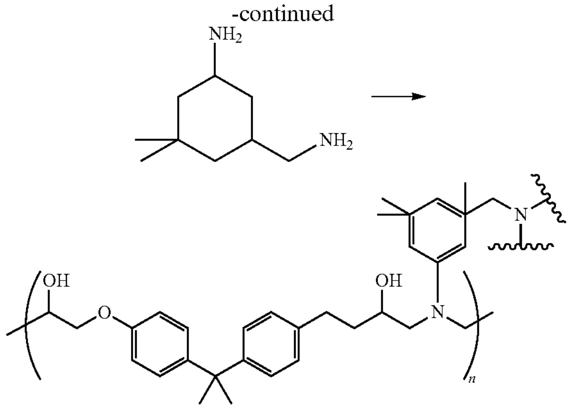

General Procedures for Model Compound Deconstruction Reactions—Microwave Vials:

0.5 mmol of a representative model compound and desired equivalents of base were weighed and directly added to a 20 mL Biotage microwave vial with a magnetic stir bar. Appropriate volumes of solvent(s) were added via a positive displacement pipette before sealing the reaction with a Biotage cap septum via an automatic crimper set to 55 percent tightness. The vial was then placed in a preheated heat block on a hot plate and reacted while stirring at 650 rpm. The vial was removed from heat after varying times. Reactions were then directly sampled with a 10 microliters positive displacement pipette to create a 100× reaction dilution with HPLC acetone for direct GC-FID quantification of products and any remaining starting material.

Model Compounds Deconstruction Reactions and Products:

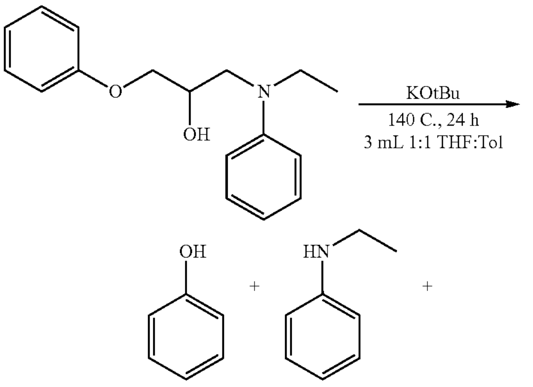

-continued

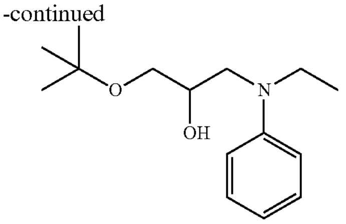

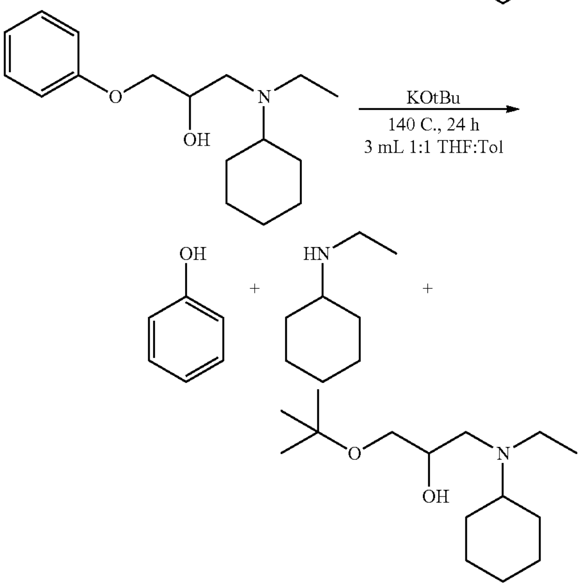

General Procedures for Thermoplastic Deconstruction Reactions—Microwave Vials:

A single amine-cured epoxy thermoplastic cube (about 200 mg, 0.5 mmol of monomer repeat units) and desired equivalents of base were weighed and directly added to a 20 mL Biotage microwave vial with a magnetic stir bar. Appropriate volumes of solvent(s) were added via a positive displacement pipette before sealing the reaction with a Biotage cap septum via an automatic crimper set to 55 percent tightness. The vial was then placed in a preheated heat block on a hot plate and reacted while stirring at 650 rpm. The vial was removed from heat after varying times. To neutralize the reaction, 3 mL of 2 M HCl in diethyl ether was added directly to the reaction vials via a positive displacement pipette. Reactions were then directly sampled with a 10 uL positive displacement pipette for a 100× reaction dilution with HPLC acetone and direct GC-FID quantification of products.

Thermoplastic Deconstruction Reactions and Products:

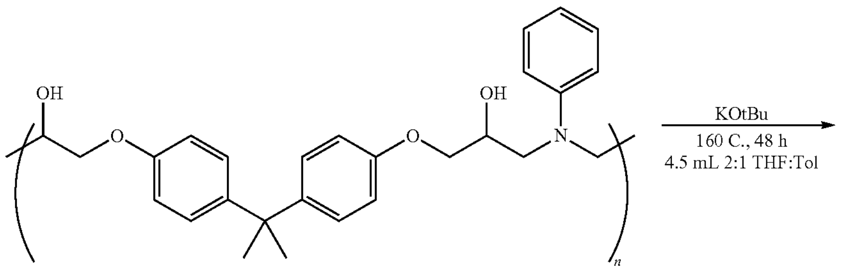

-continued

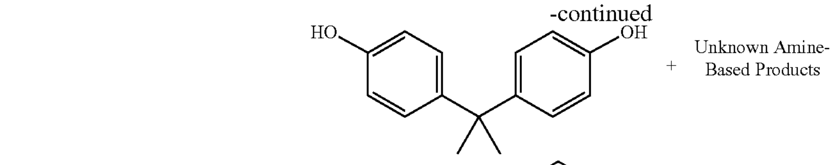

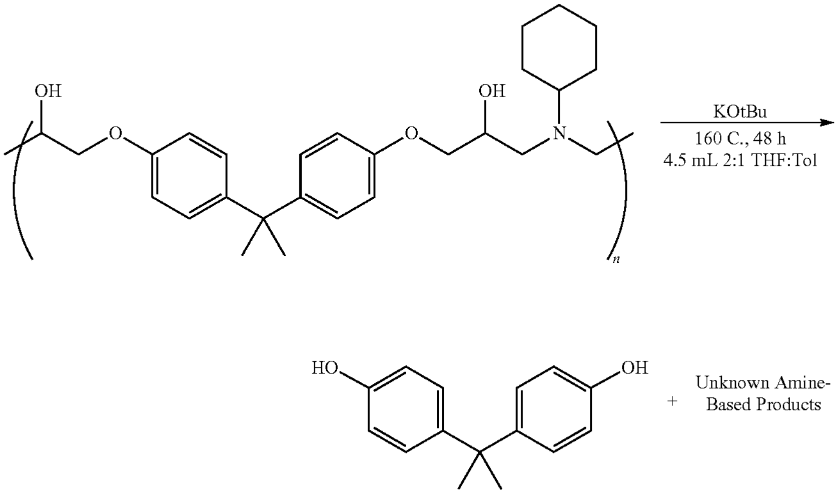

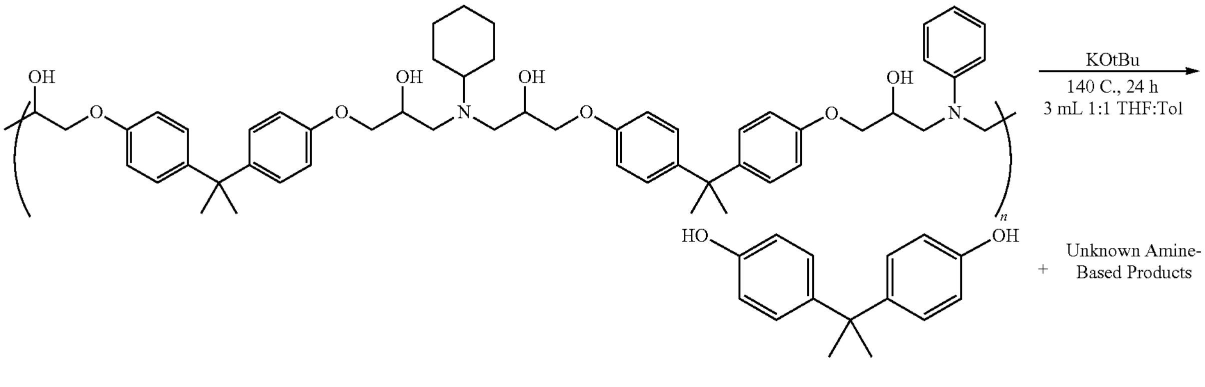

General Procedures for Thermoset Deconstruction Reactions—Microwave Vials:

Amine-cured epoxy thermoset cubes were pretreated via soaking in glacial acetic acid either in ambient conditions for varying times or in a chemical microwave for varying times and temperatures. The cube was removed from the acetic acid, rinsed with acetone, and dried for 1 hour in a vacuum oven. The dried thermoset cube and desired equivalents of base were weighed and directly added to a 20 mL Biotage microwave vial with a magnetic stir bar. Appropriate volumes of solvent(s) were added via a positive displacement pipette before sealing the reaction with a Biotage cap septum via an automatic crimper set to 55% tightness. The vial was then placed in a preheated heat block on a hot plate and reacted while stirring at 650 rpm. The vial was removed from heat after varying times. To neutralize the reaction, 3 mL of 2M HCl in diethyl ether was added directly to the reaction vials via a positive displacement pipette. Reactions were then directly sampled with a 10 uL positive displacement pipette to a 100x reaction dilution with HPLC acetone for direct GC-FID quantification of reaction products.

Thermoset Deconstruction Reactions and Products:

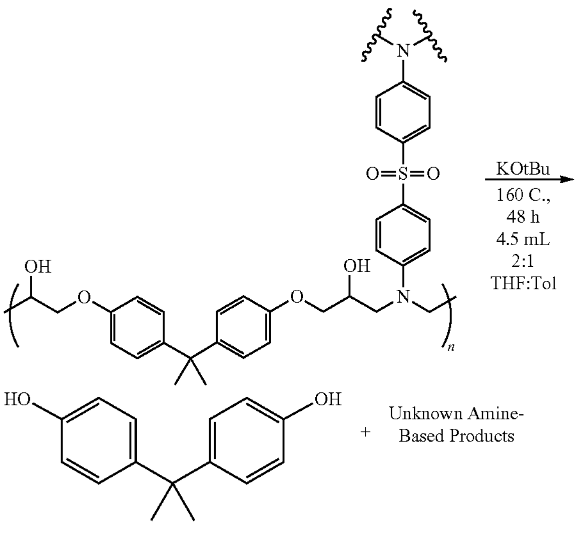

-continued

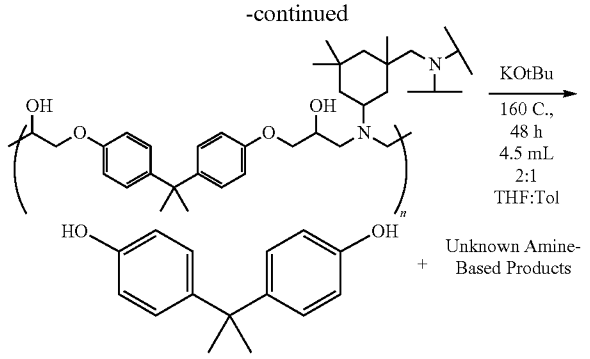

General Procedures for Model Compound Deconstruction Reactions—Sand Bath Reactors:

0.25 mmol of a representative model compound and desired equivalents of base were weighed and directly added to a 3 mL SwageLok reactor. Appropriate volumes of solvent(s) were added via a positive displacement pipette before sealing the reactor. The vial was then placed in a preheated fluidized sand bath. The vial was removed from heat after varying times and placed directly into an ice bath. Reactions were then directly sampled with a 10 uL positive displacement pipette to a 100× reaction dilution with HPLC acetone for direct GC-FID quantification of reaction products.

General Procedures for Thermoplastic Deconstruction Reactions—Sand Bath Reactors:

Half of an amine-cured epoxy thermoplastic cube (about 100 mg, 0.25 mmol of monomer repeat units) and desired equivalents of base were weighed and directly added to a 3 mL SwageLok reactor. Appropriate volumes of solvent(s) were added via a positive displacement pipette before sealing the reactor. The vial was then placed in a preheated fluidized sand bath. The vial was removed from heat after varying times. The vial was removed from heat after varying times. To neutralize the reaction, 1.5 mL of HCl in ethers was added directly to the reaction vials via a positive displacement pipette. Reactions were then directly sampled with a 10 uL positive displacement pipette to a 100× reaction dilution with HPLC acetone for direct GC-FID quantification of reaction products.

General Procedures for Thermoset Deconstruction Reactions—Sand Bath Reactors:

Amine-cured epoxy thermoset cubes were pretreated via soaking in glacial acetic acid either in ambient conditions for varying times or in a microwave for varying times and temperatures. The cube was removed from the acetic acid, rinsed with acetone, cut in half, and dried for 1 hour in a vacuum oven (at 35 degrees Celsius). The dried thermoset cube and desired equivalents of base were weighed and directly added to a 3 mL SwageLok reactor. Appropriate volumes of solvent(s) were added via a positive displacement pipette before sealing the reactor. The vial was then placed in a preheated fluidized sand bath. The vial was removed from heat after varying times. The vial was removed from heat after varying times. To neutralize the reaction, 1.5 mL of HCl in ethers was added directly to the reaction vials via a positive displacement pipette. Reactions were then directly sampled with a 10 uL positive displacement pipette to a 100× reaction dilution with HPLC acetone for direct GC-FID quantification of reaction products.

Generalized Procedure for Preparing GPC Samples

Post-reaction samples were filtered using 0.22 μm Restek syringe filters and dried via a nitrogen blower until all solvent evaporated. Dried samples were weighed and HPLC THF was added to produce samples with 10 mg/mL concentrations.

Results

Figure 2:
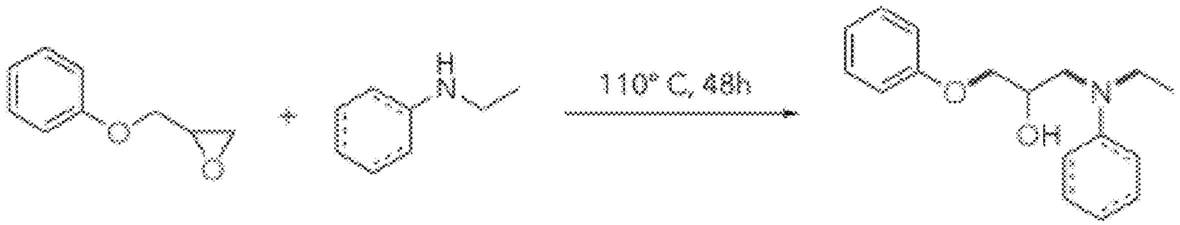
FIG. 2 depicts synthetic routes to (2) aromatic and (3) aliphatic epoxy model compounds. Bonds targeted for cleavage are highlighted in red.

We initially designed small molecules 2 and 3 (see FIG. 2), to act as model systems to reflect the C—O ethereal and C—N amino linkages in industrial epoxy amine materials. These model compounds allowed for the screening of reaction conditions for deconstruction and simple post reaction analysis. These small molecule models are straightforward to synthesize, here up to 50 g in a single batch, by combining epoxide 1 with a chosen amine partner and heating the mixture to 110° C. in the absence of a solvent. The resulting products were not purified before use in deconstruction after confirming purity by NMR and gas chromatography (GC). Starting materials and deconstruction products were quantified in a single GC experiment.

We began tested deconstruction conditions by combining our aromatic model compound 2 with a variety of oxidants and Lewis acids that highlighted oxidative C—C cleavage in other commodity plastics. These conditions all resulted in much lower product yields and/or instability of most identified amine reaction products. We moved on to homogeneous reducing agents such as $LiAlH_4$ or $NaBH_4$, no reactivity was observed in either case. Further screens shifted to 5 eq. each of a wide range of bases from different reactivity classes. We evaluated bases including KOtBu, $Cs_2CO_3$, KOH, diazabicy-cloundecene (DBU), and sodium bis(trimethylsilyl)amide (NaHMDS). Trial solvents for these base-mediated tests were toluene or ethylene glycol, as we hypothesized that bases would react well in these solvents and high boiling points would accommodate relatively high temperatures for screening. This was important as we inevitably needed to heat polymers above their $T_g$ for reactivity. The screening reaction temperature was 140 degrees Celsius, such that toluene reactions would be at a reflux and the ethylene glycol counterparts would not. Reactions were conducted in microwave vials that can withstand up to 30 bar of pressure. We qualitatively assessed reactivity for productive reactions by GC with a flame ionization detector (FID) and identified products by a combination of commercial standards, mass spectrometry, and nuclear magnetic resonance (NMR) spectroscopy analyses of isolated small molecules. We then quantitatively measured product yields for two preferred initial base classes with GC-FID via calibration curves and continued to optimize conditions below for promising bases.

Figures 3A, 3B, 3C:
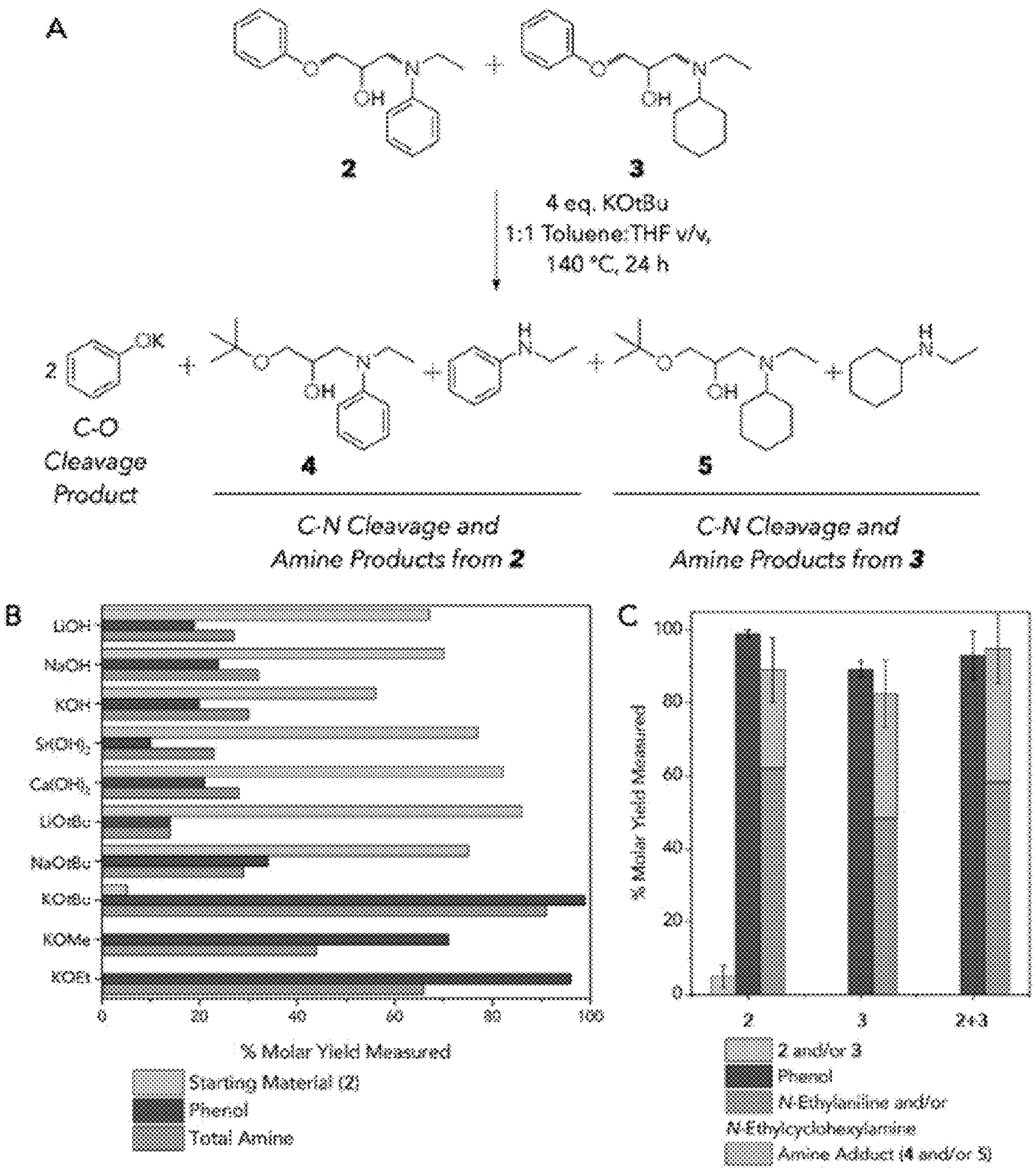
FIG. 3A depicts a reaction scheme for C—O and C—N bond cleavage in aromatic (2) and aliphatic (3) amine-based model compounds. Reaction conditions are listed to the right of the arrow (4 eq. KOtBu, 24 h at 140° C., 1:1 THF:toluene, 3 mL), bonds targeted for cleavage are shown in the starting materials in red, and C—O and C—N bonds are distinguished.
FIG. 3B depicts optimized reaction conditions as in FIG. 3A and product yields for both these model compound systems. As noted in the text, potassium phenoxide is generated in situ but is protonated during the reaction workup, and thus was measured and quantified as phenol.
FIG. 3C depicts percent molar yield measured for compounds 2 and/or 3, phenol, N-Ethylaniline and/or N-Ethylcyclohexylamine and amine adduct 4 and/or 5. These experiments were conducted in duplicate, and the error bars reflect standard deviation values.

After these initial reaction screens, only conditions in toluene generated product and only KOtBu resulted in full consumption of 2. As shown in FIG. 3, the reaction products were divided into potassium phenoxide as the sole C—O cleavage product and a combination of N-ethylaniline and amine adducts 4 or 5 as the only two identifiable amine products from 2 (see FIG. 3A). Characterization data after isolation of 4 and 5 confirmed both of their structures, allowing us to determine yields of these new compounds. Molar yields shown in FIGS. 3B and 3C reflect this separation of alcohols from C—O cleavage and all amine products.

After observing that the potassium phenoxide generated from C—O cleavage in highly basic conditions (pH about equal to 14) was not fully soluble in toluene, we transitioned the reaction solvent to a 1:1 v/v mixture of toluene:tetrahydrofuran (THF). This solvent mixture was also found to be useful for enabling polymer reactivity. For the model compounds, a 1:1 v/v mixture of toluene and THF allowed for direct sampling and yield measurements without any reaction quenching or workup needed. The potassium phenoxide could be measured and quantified with a phenol standard, as this salt becomes protonated during dilution before GC analyses to form phenol. KOtBu also generates higher yields than either sodium or lithium tert-butoxide (FIG. 3B).

When further comparing KOtBu-mediated reactivity with five different metal hydroxide bases (LiOH, NaOH, KOH, $Ca(OH)_2$, and $Sr(OH)_2$), KOtBu exhibited improved reactivity in all cases (FIG. 3B). All reactions using each of the five hydroxide bases resulted in significant starting material remaining after 24 h at 140° C., relative to full consumption using KOtBu at the same conditions. Similarly, either KOEt and KOMe generated full conversion of 2 to reaction products (FIG. 3B). Through additional reaction screening, we continued with —OtBu bases instead of their methyl, or ethyl counterparts due to similar reaction profiles but either fewer reaction side products, improved reagent robustness, and/or lower cost with its use (FIG. 3B).

Additional experimental trials investigated reaction temperatures, base equivalents, reaction volume, and reaction time. Optimized yields for bond cleavage with 2 were 99 plus or minus 1 mol percent for phenol, and 89 plus or minus 9 mol percent for total amine products (FIG. 3C, reaction conditions: 140° C., 24 h, 1:1 THF:toluene, 4 eq. of KOtBu). These reaction conditions worked similarly well with 3 (89 plus or minus 3 mol percent for phenol, 85 plus or minus 5 mol percent for total amine products (FIG. 3C). We also mixed equal ratios of 2 and 3 to highlight the ability of KOtBu to cleave C—N and C—O bonds in a combination of aliphatic or aromatic amine-containing materials. In this case, total phenol yield was 97 plus or minus 4 mol percent, and total yield of amine products was 99 plus or minus 1 mol percent (FIG. 3C).

Figure 4:
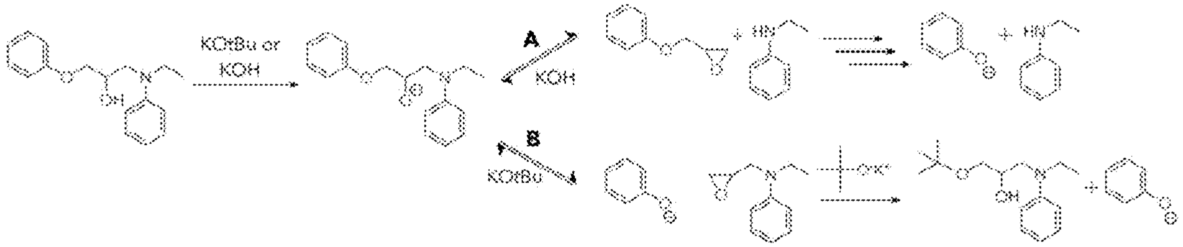
FIG. 4 depicts a proposed reaction pathway for C—O and C—N bond cleavage in epoxy model compounds. As noted in text, we identified that only alkoxide bases can access pathway B, allowing for improved yields with these reagents. In this figure, we used KOtBu as an example of an alkoxide base and KOH to represent other base classes.

Without being limited by theory, based on the products formed during the reaction, we hypothesized that these KOtBu-mediated bond cleavage events occur via an epoxide mechanism with two potential reaction pathways (FIG. 4) that occur simultaneously. Both options generate potassium phenoxide, but pathway A results in free N-ethylaniline or N-ethylcyclohexylamine and B yields amine adducts 4 or 5, depending on the starting material. Existing basic epoxy deconstruction strategies use hydroxide-type bases that can only access pathway A, while we hypothesize that reactivity through A and B concurrently leads to improved yield and stability of amine products. We assessed the validity of this proposed mechanism by treating the hypothesized intermediate epoxide 1 with combinations of KOtBu, heat, and N-ethylaniline to observe product formation. All reactions in this test occurred at 24 h at 140° C. with 1:1 v/v THF: toluene. In these control reactions, 1 did not transform with heat alone, and cleanly generated potassium phenoxide with 2 eq. of KOtBu. When combining 1 and 1 eq. of N-ethylaniline, both compounds were stable with heat, while adding 2 eq. of KOtBu produced both phenoxide and N-ethylaniline. These data are in alignment with the hypothesized reaction pathway.

Figure 5A:
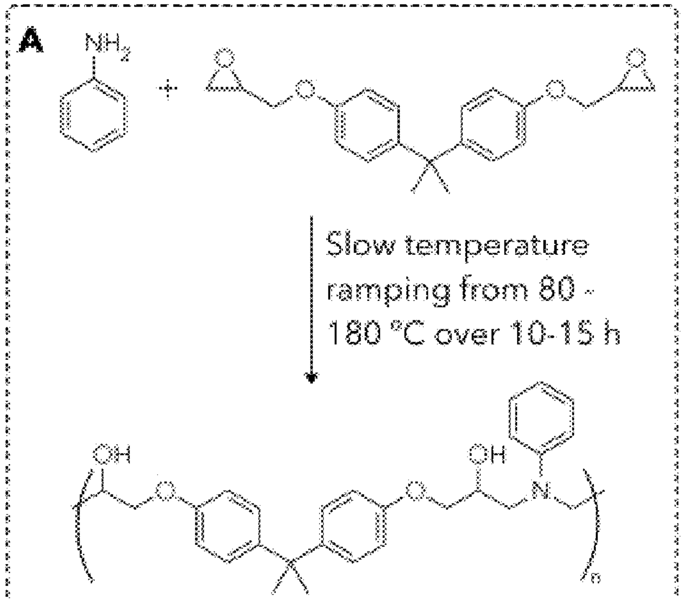
FIG. 5A depicts the synthesis of 7 as an example aromatic thermoplastic reaction scheme.
Figure 5B:
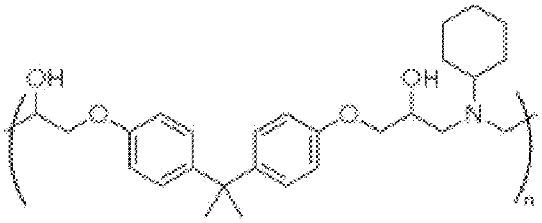
FIG. 5B depicts the synthesis of an aliphatic thermoplastic, 8.
Figure 5C:
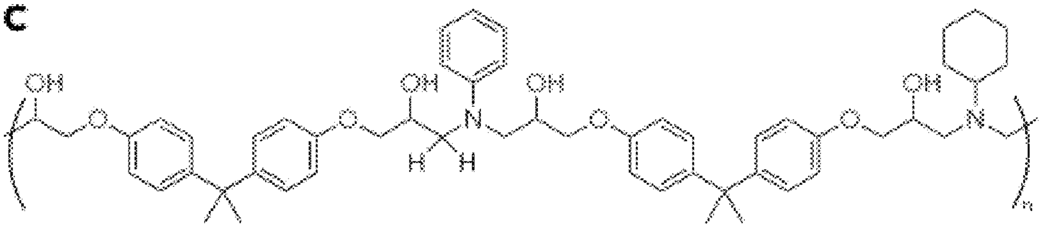
FIG. 5C depicts the synthesis of a 50:50 mixed aromatic:aliphatic thermoplastic substrate, 9. All polymers are BADGE-based, and 7 contains only an aromatic amine curing agent while 8 uses an aliphatic amine and 9 contains a 1:1 ratio of these monomers. All structures in this figure were cured in silicone trays in a variable temperature oven and used directly without any purification.

Based on the success with model compounds, we generated related thermoplastics to investigate reactivity with amine-cured epoxy polymers. We used 2,2'-(((propane-2,2-diylbis(4,1-phenylene))bis(oxy))bis(methylene))bis(oxirane) (BADGE, 6), since it is a common industrial epoxide in amine-epoxy resins (FIG. 5). Thermoplastics combine aniline and/or cyclohexylamine in 1:1 molar ratios with 6 as a diepoxide. Polymers disclosed herein are generated via curing resin mixtures in silicone trays containing 1 $cm^3$ cavities. Resultant polymer substrates are 1×1 cm cubes of about 200 mg each, where one cube is used for each deconstruction reaction test. As with the small molecule models, polymer yields were quantitative, and resultant materials allow us to separate the reactivity of aromatic and aliphatic amines in depolymerization (7 and 8). We also extended our epoxy curing strategy to a mixed aliphatic and aromatic thermoplastic containing 1:1 aniline:cyclohexylamine (9). In an embodiment, heating cycles for each of these polymers is developed based on curing data from differential scanning calorimetry (DSC).

We also used these linear polymers to enable solution-state analysis techniques before and after de-polymerization reactions, including NMR spectroscopy and gel permeation chromatography (GPC) which show $^1H$, $^{13}C$, correlation spectroscopy (COSY), heteronuclear single quantum coherence (HSQC), and infrared (IR) spectra for each compound. GPC was also used to determine molecular weight distributions for soluble polymer fractions. We supplemented these solution-state structural data with thermal information from DSC and thermogravimetric analysis (TGA) for each polymer.

We also completed solubility tests with polymers 7-9, which demonstrated that all three polymers are insoluble in toluene, trichloro-benzene, ethylene glycol, and limonene. Additionally, 7 was also insoluble in acetic acid, hexafluoroisopropanol, and N-methyl-2-pyrrolidone. In contrast, we obtained the best results in all cases with ethers such as THF or dioxane. Through structural analyses and solubility studies for each thermoplastic, we hypothesized that aromatic amine-containing materials are slightly crosslinked through the alcohol in the polymer backbone. Without being limited by theory, this crosslinking occurs with materials that have at least 75 percent aniline content due to the decreased nucleophilicity of aniline compared with cyclohexylamine. As a result, polymers with 75 or 90 percent aniline content (10 and 11, FIG. 5C) remain partly insoluble in all ten organic solvents tested with polymer 7, indicating partial crosslinking. Solution state analyses for these polymers reflect the about 50 percent soluble polymer fraction for these slightly crosslinked thermoplastics only, while thermal and IR data are reflective of the whole polymer systems.

Figures 6A, 6B, 6C:
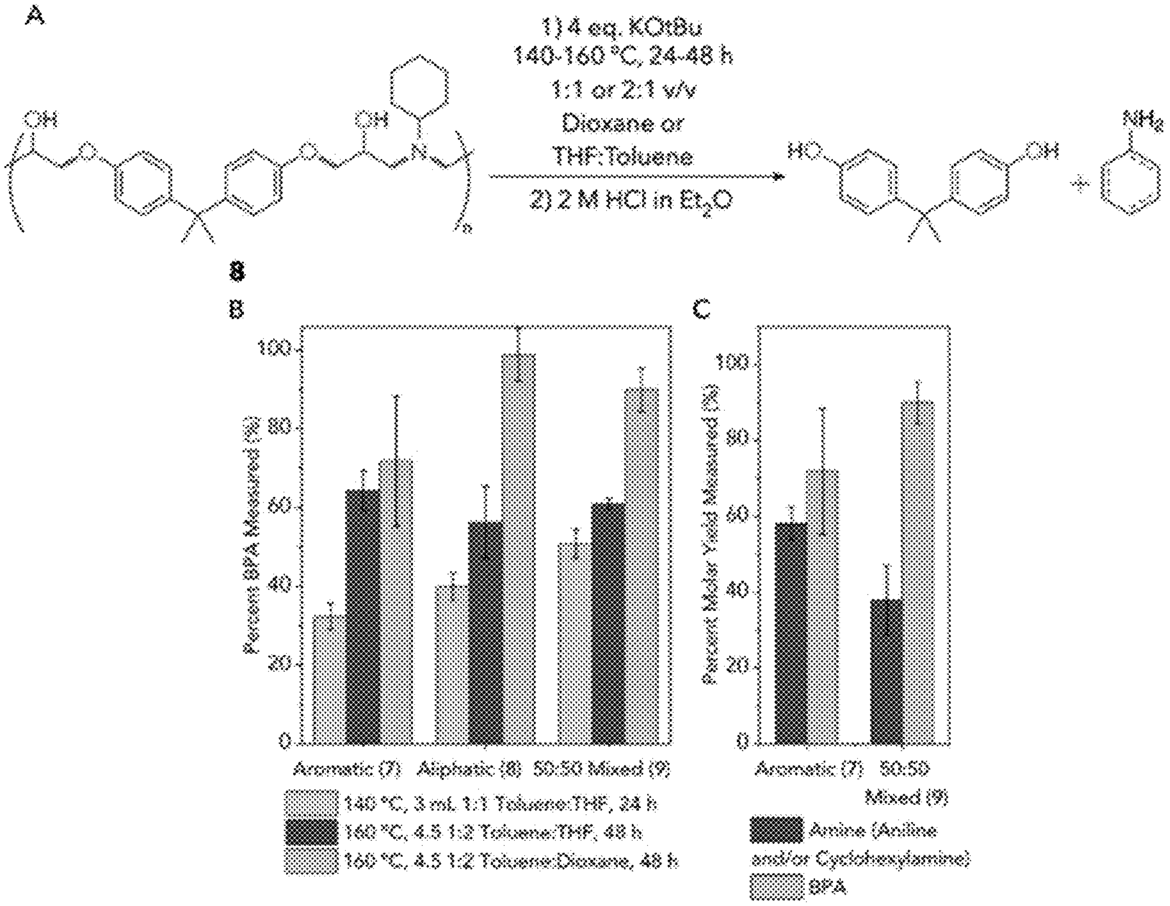
FIG. 6A depicts a sample thermoplastic deconstruction reaction.
FIG. 6B depicts thermoplastic deconstruction BPA molar yields at three different conditions. Yellow bars (left) represent optimized reaction conditions from model compounds (140° C., 24 h, 1:1 v/v THF:toluene), while the dark green bars (middle) represent partially optimized reaction conditions for thermoplastics (160° C., 48 h, 2:1 v/v THF: toluene). Optimal conditions are in light blue (right, 160° C., 48 h, 2:1 v/v dioxane:toluene). Reactions were conducted in duplicate or triplicate and error bars show standard deviation values.
FIG. 6C depicts amine (green) and BPA (blue) yields from deconstruction of aromatic amine-containing thermoplastic substrates.

The initial investigations into thermoplastic depolymerization utilized the optimized conditions from both model compounds 2 and 3 (140° C., 24 h, 1:1 toluene:THF). As shown in FIG. 6A, these reactions initially generate the di-potassium salt of bisphenol A (BPA). Upon reaction quenching with 2 eq. of 2 M HCl in ether, we directly obtained and quantified BPA (32 plus or minus 8) mol percent with 7). We confirmed the initial di-potassium salt mentioned above via a BPA stability test, where 0.5 mmol of this diol was added and reacted under desired basic conditions. We measured only 46 percent of BPA before a 2 M HCl quench, but observed 96 percent directly after this step. Reactions to optimize thermoplastic deconstruction illustrated that polymer dissolution and/or swelling must occur before bond cleavage events. As a result, reactions in toluene only were completely unsuccessful, since all polymers (7-9) would not dissolve and thus not depolymerize.

We subsequently improved our polymer deconstruction conditions through a 2:1 v/v THF:toluene ratio, maintaining a small amount of toluene for improved base reactivity and added THF for polymer solubility. We observed a large increase in BPA yields (36 to 43 mol percent with 8 as a substrate) after 48 h reaction times. In an embodiment, using cryomilled thermoplastics results in higher yields than reacting unmodified cubes, presumably due to improved surface area. We recognize that this preprocessing strategy is impractical with carbon fiber-reinforced composites, so we continued with full cubes for reactions. Further optimization relative to small molecule conditions raised the reaction temperature from 140° C. to 160° C., with corresponding yield increases with 8 from 37 to 50 mol percent. Combining all these improvements produced a 66 plus or minus 5 mol percent BPA yield from 7 (FIG. 6B).

Without being limited by theory, we propose that a solvent to maintain polymer substrate solubility during reactions with a higher boiling point that THF might improve monomer yields. To this point, we substituted 3 mL of THF for dioxane in deconstruction reactions to obtain the highest amounts of BPA for all three thermoplastics. Both THF and dioxane result in similar qualitative solubilities of starting polymers at room temperature. We propose that improved reactivities are due to the higher boiling point of dioxane as compared with THF, such that a larger proportion of this solvent was in solution at 160° C. to solubilize polymers during deconstruction. Resultant molar yields of BPA were 72 plus or minus 16 percent for 7, 99 plus or minus 7 percent for 8, and 90 plus or minus 5 percent for 9. These data did not significantly improve after increasing reaction temperatures to 180° C. Our BPA yields from thermoplastics compare with the high yields of phenol observed when reacting small molecule models. Further, our best reaction conditions for thermoplastics also resulted in significant yields of aniline after reactions (58 plus or minus 4 mol percent from 7 and 38 plus or minus 9 mol percent of total amine content from 9 (FIG. 6). Aliphatic amine components of these polymer reactions are complex oligomers and vary much more than in the small molecule reactions.

Figures 7A, 7B, 7C:
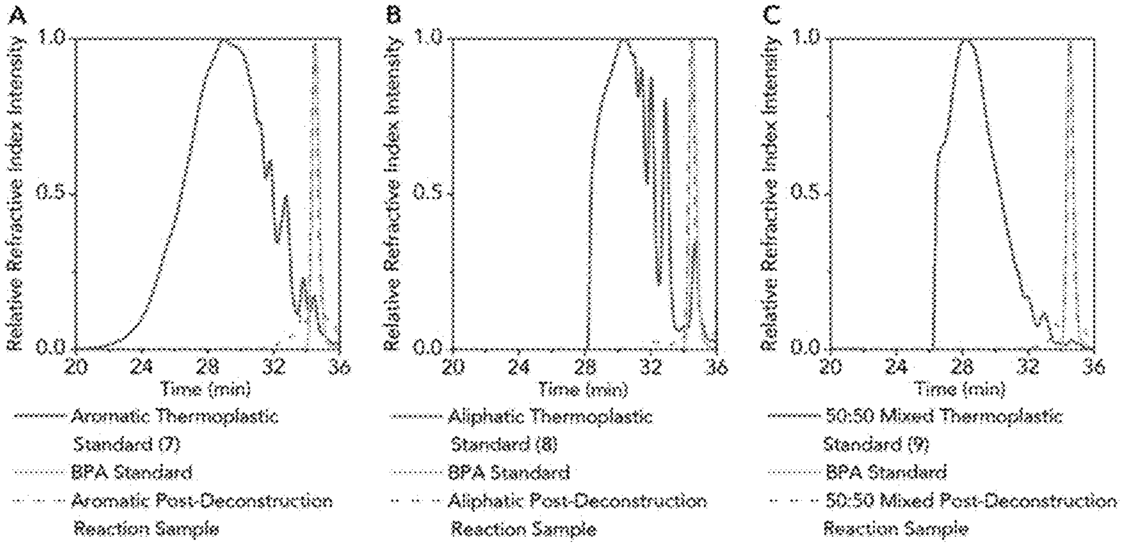
FIG. 7A depicts GPC data before and after epoxy deconstruction for aromatic thermoplastic 7.
FIG. 7B depicts GPC data before and after epoxy deconstruction for aliphatic thermoplastic 8.
FIG. 7C depicts GPC data before and after epoxy deconstruction for 50:50 mixed thermoplastic 9. In all three cases, GPC experiments were conducted in THF. Dark green traces represent thermoplastic standards before reaction, yellow traces are from a BPA standard, and light blue traces represent post-reaction analyses. The sharp peak observed in all three post-reaction samples is BPA. Amine products cannot be observed by GPC because their molecular weights are below the instrument and column resolution.

Optimized deconstruction results can also be visualized with GPC traces before and after reactions for models 7-9 (FIG. 7). The difference in post-deconstruction reaction purity between THF and dioxane-containing reactions may also be represented by GPC.

Figure 8:
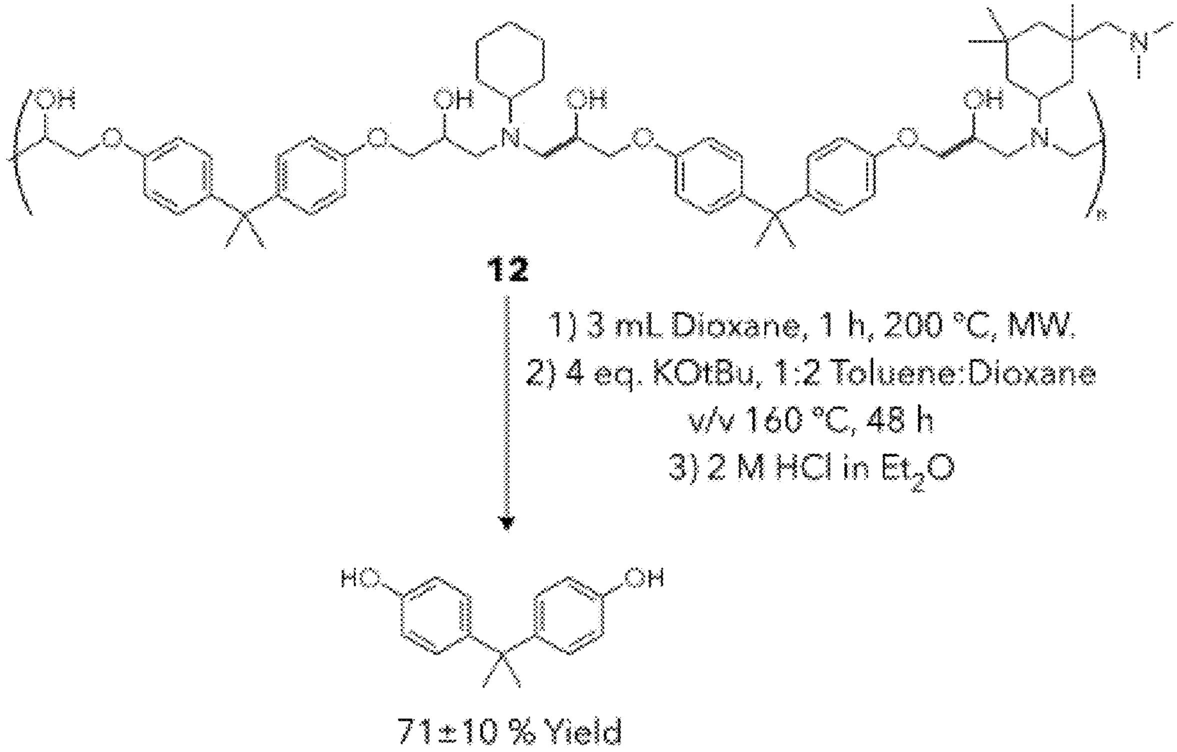
FIG. 8 depicts a deconstruction reaction using an aliphatic amine-based thermoset substrate (12). Reactions conditions were 160° C., 48 h, 2:1 v/v THF:toluene were applied from thermoplastic depolymerization work. In this figure, MW represents microwave irradiation.

To test thermoset materials, we developed thermoset 12 (FIG. 8) to replicate the thermal properties of industrial amine-epoxies that we measured from Hexion's proprietary resin combinations ($T_g$ of 85° C.). This process involved optimizing crosslink densities and ratios of monoamines to diamines in a polymer resin. We chose isophorone diamine (IPDA) as a crosslinker due to its prevalence in current industrial epoxies. Combining this amine in equal ratios with cyclohexylamine and using 6 as the sole epoxide resulted in a polymer with a $T_g$ of 105° C. (FIG. 8).

Relative to the thermoplastics described above, thermoset 12 does not dissolve in any solvent, but rather it only swelled slowly over time. Reactions with a thermoset cube and optimized conditions from thermoplastics above resulted in minimal product formation and a full cube remaining after heating. To accelerate thermoset swelling and thus improve depolymerization, we heated a cube of polymer 12 in 3 mL of either THF or dioxane for one hour at 200° C., taking inspiration from previous success with solvent choices when using thermoplastic substrates. These preswelling experiments were done in a CEM chemical microwave. After this, the cube already began to break apart into somewhat smaller and fragile, gel-like pieces but the network itself was unchanged via TGA analyses. We quantified this polymer swelling by TGA to assess solvent incorporation into the network by percent mass.

We then transferred the CEM vial contents to a Biotage microwave vial with an appropriate pressure rating, added 1.5 mL of toluene and 4 eq. of KOtBu to this post-swelling mixture and used optimized reaction conditions from thermoplastics (48 h, 160° C.) to deconstruct this polymer for a BPA yield of 71 plus or minus 10 mol percent when dioxane is used as cosolvent. This compares with 43 plus or minus 9 mol percent BPA without preswelling. As with thermoplastics above, the aliphatic amine products were not observed after thermoset deconstruction.

Finally, these results were expanded to an industrial material using EPIKOTE Resin MGS RIMR 135 and Curing Agent MGS RIMH134-RIMH-137. We combined and cured these reagents as instructed in the data sheet from Hexion to generate thermoset resin 13. Thermal data for this polymer $T_g$ equals 85° C. Applying optimized reaction conditions from 12 above (2:1 THF:tol, 100 wt percent KOtBu, 48 h, 160° C.) resulted in 15 wt percent BPA by GC-FID from this industrial epoxy amine.

Discussion

This work demonstrates a KOtBu-mediated method for epoxy amine deconstruction developed using synthesized model compounds, thermoplastics, and a thermoset. Full depolymerization of amine-epoxy resins will require C—O and/or C—N bond cleavage, and it is noteworthy that the monomers from epoxy-amine resins pose unique stability challenges, especially as probable polyaniline formation is a common issue that prevents recovery in many oxidation or acid-catalyzed strategies. In our initial oxidation reaction tests, we obtained black and somewhat insoluble material after reactions. Confirming the exact aggregate identity of this material is particularly challenging and not part of this work. Without being limited by theory, we propose that both amine and potassium phenoxide yields are consistently higher with alkoxide bases than any of their hydroxide counterparts because hydroxide bases consistently do not access products from the second reaction pathway in FIG. 4. Isolating amine adducts 4 and 5 from aromatic and/or aliphatic amine models enables trapping amines through less reactive products in epoxy deconstruction. In a prophetic example, future work aimed at recovering amine hardeners should investigate catalytic strategies that continue to stabilize these products for improved yields. Further, we highlighted reactivity using both aromatic and aliphatic amines, as industrial epoxies often contain custom ratios of different amine curing agents in proprietary ratios. It is crucial for a recycling method to address both these amine groups for applicability across composite industries.

Linear thermoplastics are useful tools in method development for epoxy depolymerization because they allowed us to separate reactivity challenges using polymer substrates from mass transfer issues associated with insoluble thermosets. These polymers were also prepared to maintain solution-state analyses before and after deconstruction reactions. We directly measured BPA and aniline after thermoplastic depolymerization reactions, substantially improving recovery of epoxy carbon content relative to existing options. This BPA and aniline content could be used to generate new BADGE to be used directly with recovered amine for newly synthesized resins or to manufacture plastics with more established chemical recycling pathways, such as polycarbonates. Versatility from products generated is important, as epoxy redesign work expands and primarily focuses on bio-based epoxides beyond only 6.

When considering thermoset reactivity, industrial thermosets we worked with often have glass transition temperatures around 110° C. and thus we designed 12 to be close to that range. The reactions with thermosets highlighted the need for swelling prior to deconstruction, such that KOtBu can effectively penetrate this connected network. Yields of these thermoset reactions can potentially be improved through reaction engineering. In an embodiment, the methods disclosed herein can be applied to carbon fiber-containing composites to assess mechanical material properties after deconstruction.

CONCLUSION

In summary, as disclosed herein, we developed an aliphatic base-mediated strategy for cleaving C—O ether and C—N amine linkages in epoxy resins. This method was developed with model compounds and expanded to linear thermoplastic polymers for high yields of BPA and aniline. Reactions with synthesized amine-cured epoxy thermoplastics then translate to a thermoset that can be deconstructed to generate high yields of BPA. This method points to a new strategy for advancing carbon fiber recovery in the future while maintaining significant carbon from the epoxy portion of composite materials.

The foregoing disclosure has been set forth merely to illustrate the invention and is not intended to be limiting.

We claim:

1. A method for metal alkoxide base-mediated cleavage of C—O and C—N bonds in amine-cured epoxy resins comprising contacting an amine-cured epoxy resin with a metal alkoxide base.

2. The method of claim 1 wherein the metal alkoxide base comprises potassium tert-butoxide.

3. The method of claim 1 wherein a metal hydroxide base is added to the metal alkoxide base wherein the metal hydroxide base is selected from the group consisting of LiOH, NaOH, KOH, $Ca(OH)_2$, and $Sr(OH)_2$.

4. The method of claim 1 wherein the cleavage of C—O and C—N bonds in amine-cured epoxy resins yields about 97 percent molar yield of phenols and about 99 percent molar yield of amine products.

5. The method of claim 1 wherein the metal alkoxide base-mediated cleavage of C—O and C—N bonds in amine-cured epoxy resins occurs at a temperature of from about 140 degrees Celsius to about 160 degrees Celsius.

6. The method of claim 1 wherein the metal alkoxide base-mediated cleavage of C—O and C—N bonds in amine-cured epoxy resins occurs in a solvent mixture of toluene and dioxane.

7. The method of claim 1 wherein the metal alkoxide base-mediated cleavage occurs over about 48 hours.

8. The method of claim 1 further comprising swelling the amine-cured epoxy resin before contacting the resin with the metal alkoxide base.

9. The method of claim 1 wherein the amine-cured epoxy resin is BADGE.

10. The method of claim 9 further comprising the step of isolating BPA and aniline as products resulting from the metal alkoxide base-mediated cleavage of C—O and C—N bonds of BADGE.

11. The method of claim 9 wherein the metal alkoxide base is potassium tert-butoxide.

12. The method of claim 9 further comprising swelling the BADGE before contacting the BADGE with the metal alkoxide base.

13. The method of claim 1 wherein the amine-cured epoxy resin is a thermoplastic resin.

14. The method of claim 13 wherein the metal alkoxide base is potassium tert-butoxide.

15. The method of claim 13 further comprising swelling the thermoplastic resin before contacting the thermoplastic resin with the metal alkoxide base.

16. The method of claim 1 wherein the amine-cured epoxy resin is a thermoset resin.

17. The method of claim 16 wherein the metal alkoxide base is potassium tert-butoxide.

18. The method of claim 16 wherein the thermoset resin has a glass temperature transition of about 110 degrees Celsius.

19. The method of claim 16 further comprising isolating resulting monomeric reaction products.

20. The method of claim 16 further comprising swelling the thermoset resin before contacting the thermoset resin with the metal alkoxide base.

* * * * *